(12) United States Patent
Hoctor et al.

(10) Patent No.: US 8,582,865 B2
(45) Date of Patent: Nov. 12, 2013

(54) ULTRASOUND IMAGING WITH RAY CASTING AND SOFTWARE-BASED IMAGE RECONSTRUCTION

(75) Inventors: Ralph Thomas Hoctor, Niskayuna, NY (US); Bruno Hans Haider, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 779 days.

(21) Appl. No.: 12/769,497

(22) Filed: Apr. 28, 2010

(65) Prior Publication Data
US 2011/0270086 A1 Nov. 3, 2011

(51) Int. Cl.
*G06K 9/00* (2006.01)

(52) U.S. Cl.
USPC ........... 382/154; 382/128; 600/443; 600/456; 600/459

(58) Field of Classification Search
USPC .......... 382/128, 154; 600/437, 440, 443, 447, 600/456, 458, 459
See application file for complete search history.

(56) References Cited

U.S. PATENT DOCUMENTS

| | | | |
|---|---|---|---|
| 5,474,073 A * | 12/1995 | Schwartz et al. | 600/456 |
| 5,720,291 A * | 2/1998 | Schwartz | 600/456 |
| 5,910,115 A | 6/1999 | Rigby | |
| 6,375,617 B1 * | 4/2002 | Fraser | 600/443 |
| 6,428,477 B1 * | 8/2002 | Mason | 600/437 |
| 6,674,430 B1 | 1/2004 | Kaufman et al. | |
| 6,676,606 B2 * | 1/2004 | Simpson et al. | 600/458 |
| 6,692,438 B2 * | 2/2004 | Skyba et al. | 600/440 |
| 6,755,787 B2 * | 6/2004 | Hossack et al. | 600/447 |
| 6,824,514 B2 * | 11/2004 | Poland et al. | 600/437 |
| 7,037,263 B2 | 5/2006 | Sumanaweera et al. | |
| 7,110,583 B2 | 9/2006 | Yamauchi | |
| 7,133,041 B2 | 11/2006 | Kaufman et al. | |
| 7,356,178 B2 * | 4/2008 | Ziel et al. | 382/154 |
| 7,529,393 B2 * | 5/2009 | Peszynski et al. | 382/128 |
| 7,537,567 B2 * | 5/2009 | Jago et al. | 600/447 |
| 7,645,237 B2 * | 1/2010 | Frisa et al. | 600/447 |
| 7,675,517 B2 | 3/2010 | Yang et al. | |
| 8,137,272 B2 * | 3/2012 | Cooley et al. | 600/437 |
| 2006/0293596 A1 * | 12/2006 | Jago et al. | 600/437 |
| 2011/0270086 A1 * | 11/2011 | Hoctor et al. | 600/443 |

FOREIGN PATENT DOCUMENTS

WO 2007002146 A2 1/2007

OTHER PUBLICATIONS

Clarice Hofstadler-Deiques et al.; "Software System for Three-Dimensional Volumetric Reconstruction of Histological Sections: A Case Study for the Snake Chondrocranium"; The Anatomical Record Part A 286A:938-044, 2005.

Accuimage et al. Clinical Image Processing Department—Software website: http://image.nih.gov/software/vis_packages.html, last visited Jul. 15, 2013; 26 pages.

* cited by examiner

*Primary Examiner* — Gregory M Desire

(74) *Attorney, Agent, or Firm* — Scott J. Asmus

(57) ABSTRACT

Systems and methods are presented for increasing the frame rate of real-time 3D ultrasound imaging. In one embodiment, the frame rate for generating a pseudo-shaded 2D projection image may be increased by controlling the image reconstruction process. Rather than beamforming, scan converting, and interpolating a 3D voxelized data set of an entire scanned volume, only samples required for generating the 2D projection image may be reconstructed. The element data measured from each transducer array element may be combined to directly reconstruct those 3D image samples required by the volume rendering algorithm to generate the 2D projection image.

19 Claims, 3 Drawing Sheets

ULTRASOUND IMAGING WITH RAY CASTING AND SOFTWARE-BASED IMAGE RECONSTRUCTION

BACKGROUND OF THE INVENTION

The subject matter disclosed herein relates to ultrasound imaging techniques, and more particularly, to software-based image reconstruction techniques.

Medical diagnostic ultrasound is an imaging modality that employs ultrasound waves to probe the acoustic properties of the body of a patient and produce a corresponding image. Generation of sound wave pulses and detection of returning echoes is typically accomplished by an ultrasound probe having an array of transducers. Such transducers typically include electromechanical elements capable of converting electrical energy into mechanical energy for transmission of ultrasonic waves into patient tissue and mechanical energy back into electrical energy when the reflected ultrasonic waves reach the transducers.

Real-time three-dimensional (3D) ultrasound is a type of imaging modality that involves transmitting ultrasonic acoustic waves into a 3D volume and reconstructing the measured echoes to display a two-dimensional (2D) rendering of the 3D reflectivity distribution of the volume. Transmitting the ultrasonic waves to a scanned volume may involve directing a transducer array to transmit ultrasonic waves in the scanned volume (e.g., a volume in a patient's body). The ultrasonic waves reflected by the scanned volume may be received by an ultrasound probe, digitized, formed into beams, and voxelized, or converted into electrical data in the form of voxels (i.e., volumetric pixels), by subsequent processing involving various electronic components. Typically, the 3D set of voxels may be processed to display the scanned volume as either multiple 2D planes or as a pseudo-shaded projection image, which may be a shaded 2D image of a plane in the scanned volume. The pseudo-shaded projection image may also be referred to as a 2.5D projection.

Some limitations in generating real-time projection images in 3D ultrasound projections may include acoustic acquisition time and the time associated with image reconstruction. For example, to display an image based on a scanned 3D volume, typical reconstruction approaches may convert element data into a 3D matrix of millions of voxels. Additionally, image reconstruction algorithms may be applied to each of the millions of voxels to correlate each voxel with a visual attribute (e.g., color, opacity, gradient). Generally, such methods may be performed to generate the pseudo-shaded projection image.

BRIEF DESCRIPTION OF THE INVENTION

One embodiment provides an ultrasound system including a probe having a plurality of transducers. Each of the plurality of transducers is configured to insonify a three-dimensional (3D) volume. The ultrasound system further includes an imaging system including circuitry configured to perform transmit beamforming to insonify the 3D volume, receive an echo response of the insonification of the 3D volume, and produce element data based on the echo response. Further, the imaging system includes memory configured to store the element data and a processor configured to use a 3D rendering algorithm. The 3D rendering algorithm is configured to select an element data subset from the element data, compute image samples from the element data subset, and reconstruct a two-dimensional (2D) image from the image samples. The 2D image includes a pseudo-shaded projection image representing a reflectivity distribution of the 3D volume.

In another embodiment, a method for generating a two-dimensional (2D) image from a three-dimensional (3D) volume using an ultrasound imaging system is provided. The method includes performing transmit beamforming on a 3D volume. Element data is generated, and a portion of the element data is selected to generate select image points. Further, the method includes reconstructing the select image points to generate the 2D image, which may be a shaded projection image Yet another embodiment provides a method for generating a two-dimensional (2D) image from a three-dimensional (3D) volume. The method includes performing transmit beamforming in the 3D volume. Element data is generated from the reflections of transmit beamforming, and the generated element data is used to generate the 2D image. The 2D image may have a variable orientation with respect to the 3D volume.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

DETAILED DESCRIPTION OF THE INVENTION

Embodiments disclosed herein involve techniques for accelerating the three-dimensional image reconstruction of ultrasound images by using a software-based ray casting approach which reconstructs only those image points which are relevant in generating a shaded projection image. More specifically, typical image reconstruction techniques involve a scan conversion and interpolation of receive-beamformed image data over an entire scanned volume. However, only certain image points of the 3D image data may actually be utilized in the generation of the shaded projection image. In one or more embodiments, a ray casting algorithm may be used to specify and search a straight line (e.g., a ray) through the element data of the scanned volume to select a subset of the element data. The search portion of the ray casting algorithm may include performing a focused reconstruction process on the stored element data to generate image points along the ray. The ray may be constructed in the direction of every image point which will be reconstructed to select the subset of the element data, which is smaller than the entire element data. Image points of the desired projection image of the volume may be generated from the selected subset. Thus, by performing a software-based volume rendering method, a portion (e.g., the element data subset) of the element data may be selected for the reconstruction of image points and the generation of the desired projection image.

Figure 1:
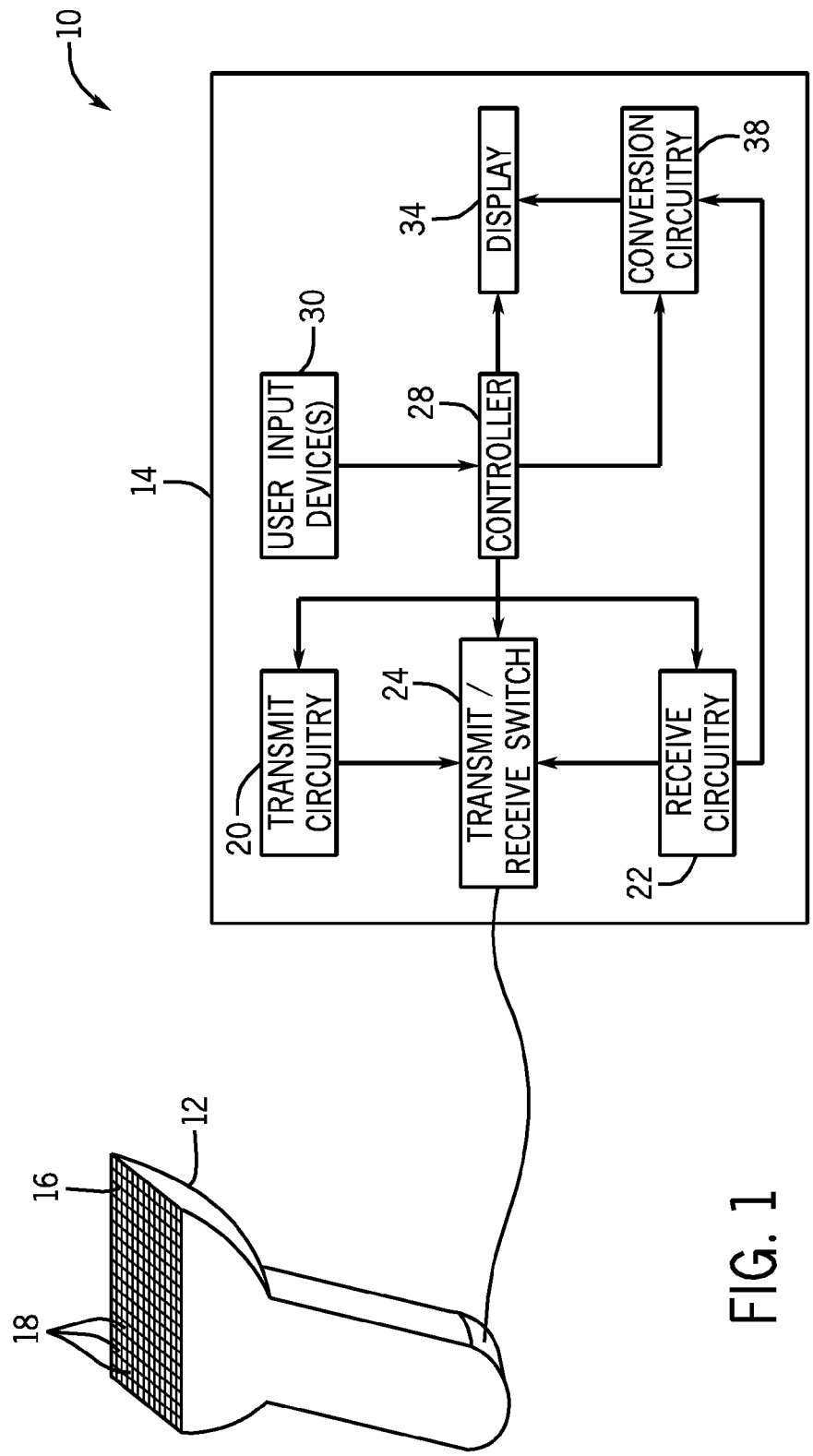
FIG. 1 illustrates an embodiment of an ultrasound data acquisition system including an ultrasound probe and an imaging system in accordance with aspects of the present disclosure.
Figure 2:
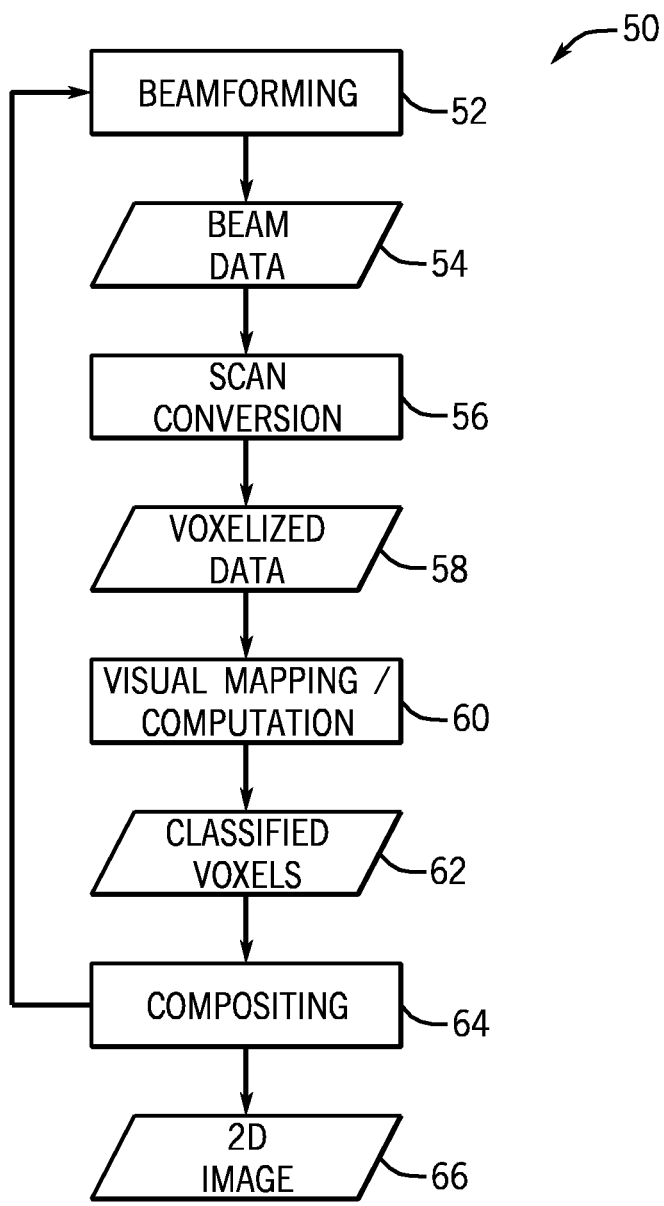
FIG. 2 is a flow chart summarizing a typical method of image reconstruction.

To provide background for typical ultrasound imaging techniques, a schematic depiction of an ultrasound data acquisition system is provided in FIG. 1, and a flow chart depicting an example of a typical ultrasound image reconstruction process is provided in FIG. 2. Turning first to FIG. 1, an ultrasonic imaging system 10 may include a variety of components, including a handheld probe 12 which is contacted with the patient during an ultrasound examination. In the depicted embodiment, the handheld probe 12 is in communication, such as via a wired or wireless communication link, with an ultrasound system or station 14 which controls operation of the probe 12 and/or processes data acquired via the probe 12.

In one embodiment, the probe 12 includes a patient facing or contacting surface that includes a transducer array 16 having a multitude of transducers 18 that are each capable of producing ultrasonic energy when energized by a pulsed waveform produced by transmit circuitry 20 within the station 14. The ultrasonic energy reflected back toward the transducer array 16, such as from the tissue of a patient, is converted to an electrical signal by the transducers 18 of the array 16. The electrical signal is communicated from the probe 12 to receive circuitry 22 of the station 14 for further processing to generate one or more ultrasound images. Operation of the transmit and receive functions of the transducers 18 may be controlled by one or more transmit/receive (T/R) switches 24 within the station 14 that control which of the transmit circuitry 20 or the receive circuitry 22 are in communication with the probe 12 at a given time.

The transmitter circuitry 20, receiver circuitry 22, and/or T/R switches 24 are operated under control of a controller 28 that may operate in response to commands received from a human operator, such as via one or more user input devices 30 (e.g., a keyboard, touchscreen, mouse, buttons, switches, and so forth). In one embodiment, the controller 28 may be implemented as one or more processors, such as general-purpose or application-specific processors, in communication with other respective circuitry and/or components of the station 14.

An ultrasound scan is performed by using the probe 12 and station 14 to acquire a series of echoes generated in response to transmission of ultrasound energy into the tissue of a patient. During such a scan, when the T/R switches 24 are set to transmit, the transmitter circuitry 20 is gated ON momentarily to energize each transducer 18. T/R switches 24 are subsequently set to receive, and the echo signals received by each transducer 18 are communicated to the receive circuitry 22. The separate echo signals from each transducer 18 are combined in the receive circuitry 22 into a signal which is used to produce a line in an image displayed on a display 34 incorporated in or in communication with the station 14.

In one embodiment, the transmit circuitry 20 may be configured to operate the array of transducers 16 such that the ultrasonic energy emitted is directed, or steered, as a beam. For example, the transmit circuitry 20 can impart respective time delays to generate temporally offset pulsed waveforms that are applied to respective transducers 18. These temporal offsets result in differential activation of the respective transducers 18 such that the wavefront of ultrasound energy emitted by the transducer array 16 is effectively steered or directed in different directions with respect to the surface of the transducer array 16. Thus, by adjusting the time delays associated with the pulsed waveforms that energize the respective transducers 18, the ultrasonic beam can be directed toward or away from an axis associated with surface of the transducer array 16 by a specified angle ($\theta$) and focused at a fixed range, R, within the patient tissue. In such an implementation, a sector scan is performed by progressively changing the time delays in successive excitations. The angle $\theta$ is thus incrementally changed to steer the transmitted beam in a succession of directions. The waveforms may be focused or unfocused, as will be discussed.

The echo signals produced by each burst of ultrasonic energy are differentially reflected by structures or structure interfaces located at successive ranges along the ultrasonic beam. The echo signals are sensed separately by each transducer 18 and a sample of the echo signal magnitude at a particular point in time represents the amount of reflection occurring at a specific range. However, due to the differences in the propagation paths between a reflecting structure and each transducer 18, these echo signals may not be detected simultaneously. Therefore, in one embodiment, the receive circuitry 22 amplifies the separate echo signals, imparts the proper time delay to each, and sums them to provide a single echo signal which represents the total ultrasonic energy reflected from a point or structure located at range R along the ultrasonic beam oriented at the angle $\theta$.

To simultaneously sum the electrical signals produced by the echoes detected at each transducer 18, time delays are introduced into the separate channels defined in the receive circuitry 22. The time delays for reception generally correspond to the time delays associated with transmission, described above. That is, the direction from which ultrasound energy is received generally corresponds to the direction in which the ultrasound energy was transmitted. However, the time delay associated with each receive channel may be adjusted or changed during reception of the echo to provide some degree of dynamic focusing of the received beam at the range R from which the echo signal emanates.

During image data acquisition, the controller 28 provides the specified delays to the receive circuitry 22 to receive echo data along the direction $\theta$, corresponding to the beam steered by the transmit circuitry 20, and samples the echo signals at a succession of ranges R so as to provide the proper delays and phase shifts to dynamically focus at points P along the beam. Thus, each emission and reception of an ultrasonic pulse waveform during an image acquisition portion of an examination results in acquisition of a series of data points which represent the amount of reflected sound from a corresponding series of points P located along the ultrasonic beam.

Conversion circuitry 38 receives the various series of data points produced by the receive circuitry 22 and converts the data into the desired image. In some embodiments, the conversion circuitry may include a graphics processing unit (GPU) having several processors (e.g., 240 processors) which may each be configured to operate in parallel. Further, each processor may operate these different algorithms associated with image reconstruction/conversion, and may be configured to operate different algorithms in parallel. In one embodiment, the conversion circuitry 38 converts the beamformed acoustic data from polar coordinate (R-$\theta$) sector format to an appropriately sized pixel data format suitable for display at a specified frame rate. The image conversion process used in some embodiments discussed herein may differ from typical image conversion processes, which also include the scan conversion of the beam data into an interpolated three-dimensional voxelized data grid. However, only a fraction of the voxels in the 3D voxelized data grid may actually be used in generating the displayed image. As will be discussed, the direct conversion of the element data (e.g., data which has not been receive beamformed) into a suitable pixel data (e.g., image data) set may reduce image reconstruction time by eliminating not only extraneous computations involved in the scan-conversion of beam data into a 3D voxelized data grid, but also the interpolation of that data into a point required by the 3D rendering algorithm.

A flow chart depicting a typical process for ultrasound imaging is provided in FIG. 2. The process 50 begins with beamforming (block 52), which may be controlled by the T/R switch 24, the transmit circuitry 20, and/or the receive circuitry 22 of the imaging system 14. Beamforming may include the generation of electronic delays for each individual transducer 18 in one or more arrays 16 for transmit and receive focusing. For example, one or more transducers 18 on a probe may be activated with different delays to image a point in a scanned volume in a patient's body. The ultrasonic waves transmitted from transducers 18 along the edge of the probe 12 may reach an image point (e.g., a point of interest in a scanning volume) later than waves transmitted from transducers near the center of the probe 12. Similarly, echoes of waves reflected from elements in the scanning volume may be received by transducers 18 along the edge of the probe 12 later than echoes received by transducers 18 at the center of the probe. The delays implemented by beamforming (block 52) may achieve transmit and receive focusing for a particular image point. Typically, a receive beamformer may produce a voxelized data set, or a three dimensional set which estimates the reflectivity of each voxel in the set.

Beam transmissions may be focused, unfocused, or weakly focused. For multi-line acquisition (MLA), the transmit may be weakly focused or unfocused, and multiple data lines of reflected waves may be formed for a range of look directions within a broad region of the scanned volume. In some systems, when transmissions are unfocused or weakly focused, a suitable processor may be used to perform scanline emulation to synthesize a focused transmission from multiple unfocused transmissions steered in different directions. Furthermore, the transmitted beams may not be uniform, and may converge at a focal range, and subsequently diverge, and in some embodiments, the converging and diverging portions of different focused beams may also be used in scanline emulation. Such methods of synthetic focusing may generally involve summing the echoes returned from multiple wave transmissions in a phase-sensitive operation to synthesize the effect of a relatively higher focused transmission. As will be discussed, MLA and synthetic focusing techniques may be used to reduce acoustic acquisition time.

The ultrasonic wave echoes received at the transducers 18 may be element data, which may correspond to measurements received at each transducer 18 of the probe 12. Element data may be in the form of radio frequency (RF) data or in-phase and quadrature (I/Q) data. Typical beamforming (block 52) processes involve receive beamforming, which converts element data into beam data 54. In typical ultrasound image techniques, the beam data 54 may then be scan converted (block 56) into voxelized data 58. Voxelized data 58 may be a digitalized rectilinearly sampled volumetric amplitude data, which may be obtained by an interpolation of the beam data 54. The interpolation may typically be tri-linear, or linear in range and in two angle dimensions.

Once the voxelized data set 58 is computed, visual attributes may be mapped (block 60) to each voxel in the voxelized data set 58. More specifically, color and opacity mapping and gradient computation may be performed for each voxel. Color mapping may involve assigning a color classification to a voxel based on the light emission of each voxel, and is typically a monotonic mapping of the amplitude at each voxel. Opacity mapping may involve computing a transparency of the amplitude data, or an ability to see through the amplitude data, and may typically result in a piecewise linear transform of the amplitude data. Such a piecewise linear transform may typically result in the amplitude ranges of some voxels being near zero, such that some features of the voxelized data set 58 appear invisible in the projection image. Gradient computation may typically be performed on each voxel by estimating the directional derivative of the amplitude distribution at each voxel in each of three orthogonal dimensions, which may be the rows and columns of the three-dimensional voxelized data set 58.

The voxelized data set 58 which includes color, opacity, and gradient estimates at each voxel may be referred to as the classified voxel set 62, which may be composited (block 64) to generate a two-dimensional image 66 based on a three-dimensional structure(s) in the scanning volume. The process of compositing (block 64) includes ray-casting, which involves traversing a pre-defined line though the classified voxel set 62 based on an output image pixel (e.g., in the 2D image 66). The interpolated values of the color and opacity along the pre-defined ray may be composited (block 64), or combined based on equation (1) below:

$$\left. \begin{array}{l} C_{j+1} = C_j + c(x_j)\alpha(x_j)(1-\alpha_j) \\ \alpha_{j+1} = \alpha_j + (1-\alpha_j)\alpha(x_j) \end{array} \right\} \text{ for } j = 1, \ldots, j_{max} \quad (1)$$

which recursively defines a pixel color $C_{j+1}$ for the next voxel in the classified voxel set 62 along the ray, and the current accumulated opacity $\alpha_{j+1}$ for the ray may defined at the $j^{th}$ point along the ray. The final value of the output pixel color of the 2D image 66 is represented by $C_{j_{max}}$. In equation (1), $x_j$ represents a location along the ray for which the values of $Cj$ and $\alpha_j$ have already been computed, and $C_{j+1}$ and $\alpha_{j+1}$ are new values that will be used at the $j+1^{st}$ point. The quantity $\alpha(x_j)$ is the interpolated opacity data at location $x_j$ in the classified voxel set 62, and $\alpha(x_j)$ is the interpolated color data at that location $x_j$. Both $\alpha(x_j)$ and $\alpha(x_j)$ may be derived from the amplitude data of the classified voxelized set 62 using a typical approach such as tri-linear interpolation. The current accumulated opacity $\alpha_{j+1}$ may be close to unity when otherwise visible features of the amplitude volume are hidden behind other features which have been classified as opaque from one point of view. As such, no modification may be performed on the output pixel color of the 2D image 66 for such features.

The gradient estimates computed for the classified voxels 62 may be used with an illumination model and an assumed light direction to provide pseudo-shading to the 2D image 66 to create the illusion of depth in the image 66. One example of a suitable illumination model used to generate shading for the image 66 may be the Phong illumination model, which provides shading and the impression of depth by introducing an artificial light source. The shading on the image 66 is created by initially modifying the color of a sample according to the illumination direction. Three types of reflected illumination, ambient light, diffuse reflection, and specular reflection, may be used in the computation, and the computed color at each point as modified by the illumination is the sum of the color modifications due to the three types of illumination. This concept may be illustrated by the Phong equation, provided below as equation (2):

$$C_o = C_a k_a C + C_P(k_d(N \cdot L) + k_s(R \cdot V)^n)C \quad (2)$$

where C is the color derived from the amplitude data, $C_o$ is computed output color used in the ray casting opacity accumulation given by equation (1), $C_a$ is the color of the ambient light, $C_P$ is the color of the point source of light "illuminating" the scene, $k_a$ is the ambient reflection coefficient, $k_d$ is the diffuse reflection coefficient, and $k_s$ is the specular reflection coefficient. N is the unit normal vector at the current point along the ray, L is a unit vector pointing in the direction of the point illumination source from any point along the ray, R is a unit vector pointing in the direction of the specular reflection at any point along the ray, and V is a unit vector pointing towards the viewer and n is the specular reflection exponent, which controls how "spread out" the specular reflection looks. The relative contributions of the ambient light, the diffuse reflection, and the specular reflection of the illumination are controlled by the coefficients of the three types of illumination. The inner product between the normalized vectors N and L is the cosine of the angle between the local gradient and direction of the light source. The inner product between the normalized vectors R and V is the cosine of the angle between the Snell's law reflection direction and the viewing direction. L and V are pre-defined for any given projection image. N is the normalized gradient vector computed from the amplitude data, and R is derived from N and L by Snell's law. In different types of medical imaging modalities, and in accordance with embodiments herein, different types of illumination types may be used. For example, the specular component may not typically be used for pseudo-shading of certain medical images. Furthermore, the Phong equation is only one example of an algorithm that may be typically used for generating shading in a 2D image 66. In some embodiments, different algorithms may also be used.

Therefore, to generate a final 2D image 66, a typical ultrasound imaging process 50 may involve many steps in the reconstruction of each voxel generated in the voxelized data set 58. However, if not every generated voxel is relevant in producing the 2D image 66, the scan conversion (block 56) and the visual mappings and computations (block 60) performed on the entire element data set 54 may take unnecessary time in the voxelizing, saving, and reconstructing of entire voxelized data set 58. Taking additional time in reconstructing unnecessary voxels may increase the image reconstruction time and reduce the image reconstruction frame rate, thus slowing the responsiveness of a full-frame-rate presentation of volumetric data in an ultrasound system 10.

As discussed, the frame rate for ultrasound imaging may be limited by image reconstruction time (e.g., the time taken to perform scan conversion and/or computations on each voxel to generate the displayed 2D image) and acoustic acquisition time (e.g., the time for an ultrasound wave to propagate through the scanning volume, be reflected by elements of the scanning volume, and propagate to be received at a transducer). In one or more embodiments, image reconstruction time may be adjusted such that it is not a limiting factor in reaching a desired frame rate. More specifically, acoustic acquisition time may be reduced to a point which supports a desired frame rate by using, for example, synthetic focus imaging techniques or multi-line acquisition, as previously discussed. Once acoustic acquisition time is reduced to support a desired frame rate, image reconstruction time may further be reduced to equal the acoustic acquisition time. Further, an acceptable image quality may be maintained.

For example, if a scanning volume were 16 cm by 6 cm by 6 cm, the scanning volume may be voxelized in cubic voxels of 0.5 mm per side (e.g., using a 3 MHz probe), which would produce about 4.6 million voxels. Using a graphics processing unit having multiple processors (e.g., 240 processors) for image reconstruction (e.g., NVIDIA® GTX285) and allowing for axial filtering, the average reconstruction time for each voxel may be approximately 0.081 ms. Reconstructing one quarter of the voxels may take approximately 98 ms, which gives a frame rate of 10 frames per second (fps). Reconstructing more voxels, for example all 4.6 million voxels, may take approximately 373 ms and give a frame rate of approximately 2.7 fps. Similarly, reconstructing less than a quarter of the voxels, for example an eighth of the voxels, may take less than 49 ms and give a frame rate of approximately 20 fps.

Assuming that the volume is insonified by 190 transmissions, and reconstructions are performed by one-way beamforming and synthetic aperture techniques, a frame rate of 25 fps may be achieved on the basis of acoustic acquisition time. In other words, if imaging were limited only by the acoustic acquisition time and not by the image reconstruction time, an ultrasound system using similar parameters as those discussed above may potentially reach a 25 fps frame rate. In some embodiments, image reconstruction time may be reduced to enable a frame rate equal to the frame rate based on acoustic acquisition time. For example, to reduce the frame rate of image reconstruction to 25 fps, image reconstruction time may be approximately 40 ms. In embodiments disclosed herein, image reconstruction time may be reduced by reducing the number of voxels which are reconstructed. For example, voxel reconstruction time may be reduced while maintaining image quality by focusing reconstruction on only the voxels utilized for generating the displayed image.

Figure 3:
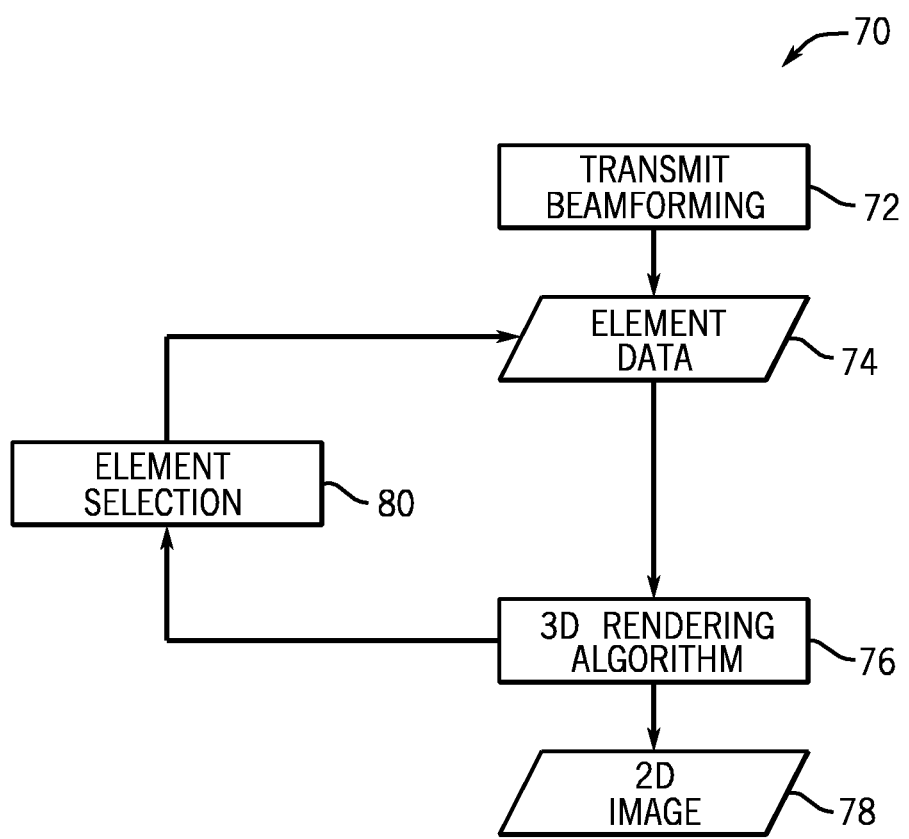
FIG. 3 is a flow chart summarizing a method of image reconstruction driven by ray casting algorithms, in accordance with aspects of the present disclosure.

A flow chart depicting an imaging process for selectively reconstructing samples utilized for generating a desired two-dimensional pseudo-shaded image of a three-dimensional scanning volume is provided in FIG. 3. Samples may refer to image points reconstructed from selected element data. Though both samples and voxels may generally refer to image data, the present disclosure may differentiate samples from voxels based on the format in which each sample or voxel are generated and/or processed. For example, voxels may refer to volumetric image points or volumetric pixels stored in a three-dimensional rectilinear data set. Samples may refer more broadly to image points which are not necessarily be stored in a 3D data set.

The process 70 may begin with transmit beamforming (block 72). The hardware aspect of transmit beamforming (block 72) may include transmitting ultrasound pulses from multiple transducers 18 of one or more transducer arrays 22 of an ultrasound probe 12 (FIG. 1) into a scanning volume (e.g., a volume in a patient's body). Delays may be implemented, either via hardware or software, such that the ultrasonic transmissions from each transducer 18 may be combined to form a wavefront (e.g., the combined transmissions from each transducer 18) which propagates in a look direction, or a desired direction in the scanned volume.

In one or more embodiments, transmit beamforming (block 72) may generally be controlled by suitable circuitry (e.g., the transmit circuitry 20 and/or controller 28 (FIG. 1) which operate transmit beamforming (block 72) to insonify the volume (e.g., by transmitting beams in an open loop manner). Transmit beamforming (block 72) may include focused, unfocused, or weakly focused ultrasonic waves transmitted into the volume. When pulse transmissions are unfocused or weakly focused, synthetic focusing techniques may be applied to sum the echoes returned from multiple wave transmissions in a phase-sensitive operation and synthesize the effect of a relatively higher-focused transmission.

The waves transmitted by transmit beamforming (block 72) may be reflected by elements in the scanning volume and/or by interfaces between elements having different acoustic impedances. The reflected waves, also referred to as echoes, may propagate back toward the probe 12 to be received at the transducers 18. The data received at the transducers 18, referred to as element data 74, may be measurements of the intensity of the echoes received at each transducer 18 with respect to time. The element data 74 may be in the form of radio frequency (RF) data, which may be sampled at a relatively high rate (e.g., 40 MHz) by the transducers 18, or the element data 74 may be converted into a lowpass, complex-valued representation referred to as in-phase and quadrature (I/Q) data, which may be sampled at a relatively lower rate (e.g., 10 MHz). In some embodiments, the element data 74 may be stored as frames including a set number of transducer transmissions (e.g., 100 transmissions), and a set number of frames of the element data 74 may be buffered at one time. In other embodiments, a pre-determined number of transmissions may be buffered iteratively. The buffering of the element data 74 may be based on a configuration of the ultrasound system 10 (FIG. 1), a desired frame rate, and/or a desired image quality.

While typical imaging processes 50 (FIG. 2) may use receive beamforming to generate beam data (e.g., beam data 54 in FIG. 2) and scan conversion to convert the beam data into an interpolated rectilinear voxelized data set, such techniques may increase image reconstruction time. In embodiments disclosed herein, any point in the scanned volume may be searched and selected using a volume rendering algorithm (block 76), also referred to as a 3D rendering algorithm or a ray casting algorithm. More specifically, the 3D rendering algorithm (block 76) may be used to select (block 80) and sample the element data 74 to reconstruct a pixel which will be utilized in generating the desired image. Selecting (block 80) the element data 74 may include focusing on an image point in the volume for reconstructing the desired projection image. For example, certain receive beamforming techniques and synthetic aperture beamforming techniques may be used. The element data 74 selected (block 80) by the 3D rendering algorithm (block 76) may be reconstructed based on a transducer at which the element data 74 is received and a time during which the element data 74 is received. Because the element data 74 is not interpolated or associated with any direction, the selected element data 74 may be reconstructed by the ray casting algorithm (block 76) from any orientation. In some embodiments, as the element data 74 may be stored in memory, and the element data 74 may also be reconstructed in any order.

The 3D rendering algorithm (block 76) of the element data 74 may include the general process of reconstructing element data 74 to output the 2D image 78, and may include sampling/digitizing, other processing techniques, mapping of visual attributes, computing gradients, compositing, and/or other aspects of volume rendering and ray casting techniques the image 78. However, rather than utilizing the pipelined approach of typical volume rendering techniques, the 3D rendering algorithm (block 76) of embodiments disclosed herein may involve reconstruction of sampled element data as each sample is generated. For example, the color mapping and opacity mapping procedures, which may be similar to those in typical imaging processes (block 60 of FIG. 2), may be performed on each reconstructed sample as it is produced. The vector gradient computations may involve determining a local scalar directional derivative of gradient values based on the direction of the light source and two orthogonal directions in the plane orthogonal to the light source direction.

Additionally, the 3D rendering algorithm (block 76) may also include second harmonic imaging techniques. For example, before the element data 74 is reconstructed, in some embodiments, the element data 74 may be filtered to remove portions of the element data 74 having the fundamental frequency of the transmitted waveforms. The resulting data (which may also be represented by the element data 74 of FIG. 3) may include data corresponding to echo energy at twice the fundamental frequency of the transmitted waveform, and may generate an image from the strongest features generated by nonlinear effects of acoustic propagation.

Thus, a software-implemented 3D volume rendering algorithm in some embodiments may provide flexibility in image reconstruction, and may also reduce overall image reconstruction time. In some embodiments, eliminating the scan-conversion of element data may increase the flexibility of image reconstruction in comparison to traditional reconstruction approaches. In traditional approaches, scan conversion may result in an interpolated data set which may already include a color, opacity, and gradient estimate at each voxel based on an orientation selected in scan conversion. However, performing image reconstruction directly on the element data 74 may enable the reconstruction of any sample from any orientation in the element data 74.

Overall image reconstruction time for reconstructing a frame of the 2D image 78 may be reduced as fewer samples may be reconstructed. Generally, the samples utilized for reconstructing a desired image may be fewer than all possible voxels produced from a scanning volume (e.g., voxelized data set 58 in FIG. 2). Further, in some embodiments, the standard scan-conversion (e.g., block 56 in FIG. 2) and interpolation of voxels used in typical imaging processes may be eliminated. Elimination of interpolation may eliminate errors caused by interpolation and may also decrease computation time, thereby decreasing image reconstruction time. By selectively focusing on image points to reconstruct samples used for generating the final 2D image 78, embodiments disclosed herein may increase frame rate and/or accuracy in a real-time 2D display 78 of the 3D scanned volume.

Imaging frame rate may be further increased in accordance with one or more embodiments. For example, in one embodiment, "empty space" may be skipped. Empty space may refer to regions of the insonified volume having low received echo energy. The low energy regions may correspond with regions of blood (e.g., in a heart ventricle) which do not include structures or tissues of interest. In some embodiments, a range gate including some number of image points along a ray (e.g., 8 or 16) may be predefined. The range may be associated with a certain set of receive measurements, and data at each transducer 18 may be computed to determine whether an image point is within the range gate. If the energy computed at a transducer is below a threshold energy level, then all ray samples within the range gate may be skipped or set to zero in the compositing operation. If non-negligible energy (i.e., energy above the threshold) is found, then the range gate may be divided into a number of smaller range gates, and the energy may again be computed.

In some embodiments, computations on samples along a ray may be terminated if the accumulated opacity along a ray approaches 1, using the previously discussed opacity equation (1). When the accumulated opacity value approaches unity, the pixel color may not change, and further compositing steps may not be necessary for additional points along the ray. By using empty space skipping, early ray termination, or a combination of such techniques, only samples having strong image features may be computed.

Additionally, gradient computations may also be optimized in some embodiments. The gradient value of each sample is estimated by taking directional derivatives which is a projection of the gradient onto a basis vector in three-dimensional space. Typically, using a standard imaging process (e.g., process 50 of FIG. 2), the gradient may only be computed in the basis directions of the voxelized data set. However, using software-based ultrasound reconstruction, the vectors on which gradient projection is to be estimated may be oriented in any direction, as image reconstruction may be performed at any point in the scanned volume. Referring again to equation (2), the computation of the inner product (N·L) may be simplified by selecting a light direction, L, as one of the directions in which to compute a directional derivative. The value of the directional derivative is equal to ($\tilde{N}$·L), where $\tilde{N}$ is the unnormalized gradient (as compared to N as the normalized gradient in equation (2)). To obtain a desired value cos(θ)=N·L, the norm of the gradient may be estimated using equation (3) below:

$$\cos(\theta) = \frac{(\tilde{N} \cdot L)}{|\tilde{N}|} \quad (3)$$

The directional derivative for the light direction may be represented by the numerator in equation (3). If the directional derivative for the light direction is below a pre-set threshold, cos(θ) may be set to zero. If the directional derivative for the light direction is not below the threshold, the other two directional derivatives may be computed. Using three directional derivatives in a set of directions that span a three-dimensional space, either the norm operator may be estimated, or the square root function may be computed using a truncated series. Either approach may be an estimate of the magnitude of the gradient.

In some embodiments, a target frame rate (e.g., 25 fps) may be achieved by reducing the computation time for reconstruction of the pseudo-shaded projection image (e.g., image 78 in FIG. 3) by a factor of approximately one third to one quarter. As many of the computations discussed herein may use data-dependent steps in the reconstruction process, many processes may be performed in parallel on a graphics processing unit with one or more processors. For example, to implement certain approaches such as the gradient computation in any direction, data from other processes such as range gate energy computations, sample reconstruction and mapping to opacity and color, and compositing with early ray termination may be used. Such other processes may be run in parallel.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. An ultrasound system, comprising:
a probe comprising a plurality of transducers configured to insonify a three-dimensional (3D) volume; and
an imaging system comprising:
  circuitry configured to:
    insonify the 3D volume;
    receive an echo response of the insonification of the 3D volume; and
    produce element data based on the echo response;
  a first memory configured to store the element data; and
  a processor configured to use a 3D rendering algorithm configured to determine at least one straight line through the 3D volume, identify a set of image points along the straight line that correspond to a visible portion of a two-dimensional (2D) projection image, generate image data corresponding to the identified set of image points from the element data, and reconstruct the 2D projection image using the generated image data.

2. The system of claim 1, wherein the processor is configured to reconstruct 3D image data by performing one or more of receive beamforming, synthetic transmit focusing, multiple line acquisition (MLA), and scanline emulation on the set of image points.

3. The system of claim 1, wherein the processor is a graphics processing unit (GPU) comprising a plurality of processors capable of operating in parallel.

4. The system of claim 1, wherein the 2D image comprises a variable orientation with respect to the 3D volume.

5. The system of claim 1, wherein the 2D image is a substantially real-time representation of the 3D volume.

6. The system of claim 5, comprising a display configured to display the substantially real-time representation of the 3D volume at a frame rate of approximately 25 frames per second.

7. The system of claim 1, wherein the imaging system is configured to generate one frame of the 2D image in substantially a same amount of time as an acoustic acquisition time for producing the element data corresponding to the one frame.

8. The system of claim 1, comprising a second memory configured to store one or more of a gradient computation algorithm, an empty space skipping algorithm, and an early ray termination algorithm.

9. The system of claim 1, wherein the processor is configured to perform an empty space skipping algorithm configured to:
estimate an empty region comprising low energy in the element data; and
skip the empty region, wherein skipping the empty region comprises not computing image points from the empty region.

10. The system of claim 1, wherein the processor is configured to perform an early ray termination algorithm configured to:
compute an accumulated opacity value of the element data; and
stop computation of image points for some of the element data based on the accumulated opacity value.

11. A method for generating a two-dimensional (2D) image from a three-dimensional (3D) volume using an ultrasound imaging system, the method comprising:
insonifying a 3D volume to generate element data;
identify a set of image points along a straight line through the 3D volume, wherein the image points correspond to a visible portion of a 2D projection image; and
reconstructing the image points using the element data to generate the 2D projection image, wherein the 2D image comprises a shaded projection image.

12. The method of claim 11, wherein generating the image points comprises synthesizing a focus by delaying and combining the portion of the element data.

13. The method of claim 12, wherein the synthesized focus comprises a plurality of unfocused transmissions or a converging portion and a diverging portion of a plurality of focused beams.

14. The method of claim 11, comprising using an empty space skipping algorithm configured to estimate an empty region comprising low energy and configured to skip the empty region, wherein skipping the empty region comprises not performing beamforming or synthetic focusing on a portion of the element data corresponding to the empty region.

15. The method of claim 11, comprising using an early ray termination algorithm when an accumulated opacity corresponding to an image point along the straight line approaches unity, wherein the early ray termination comprises not performing beamforming or synthetic focusing on additional image points following the image point along the straight line.

16. The method of claim 11, comprising using a gradient computation algorithm to estimate gradient projection of the transmit beam data in any orientation with respect to the 3D volume.

17. A method for generating a two-dimensional (2D) image from a three-dimensional (3D) volume, the method comprising:
    insonifying the 3D volume to generate first element data;
    determining at least one straight line through the 3D volume;
    identifying a set of image points along the straight line that correspond to a visible portion of a two-dimensional (2D) projection image;
    generating image data corresponding to the identified set of image points from the element data; and
    generating the desired 2D projection image using the image data, wherein the desired 2D image comprises a pseudo-shaded projection image representing a reflectivity distribution of the 3D volume.

18. The method of claim 17, wherein the 2D image comprises a variable orientation based on user-specified parameters.

19. The method of claim 17, wherein generating the 2D image comprises one or more of sampling, digitizing, color mapping, opacity mapping, gradient computations, and ray casting.

* * * * *